(12) United States Patent
Kim et al.

(10) Patent No.: US 8,657,761 B2
(45) Date of Patent: Feb. 25, 2014

(54) APPARATUS FOR INSERTING NEEDLE

(75) Inventors: Kwang-Gi Kim, Gyeonggi-do (KR);
Soo-Hyeon Kim, Gyeonggi-do (KR);
Hyung-Tae Kim, Gyeonggi-do (KR)

(73) Assignee: National Cancer Center (KR)

( * ) Notice: Subject to any disclaimer, the term of this patent is extended or adjusted under 35 U.S.C. 154(b) by 762 days.

(21) Appl. No.: 12/796,446

(22) Filed: Jun. 8, 2010

(65) Prior Publication Data
US 2011/0152717 A1    Jun. 23, 2011

(30) Foreign Application Priority Data

Dec. 17, 2009    (KR) .................. 10-2009-0125831

(51) Int. Cl.
*A61B 19/00*    (2006.01)
*A61B 17/14*    (2006.01)
*A61B 17/32*    (2006.01)
*A61B 17/34*    (2006.01)
*A61B 10/00*    (2006.01)
*A61B 5/00*    (2006.01)
*B65D 81/00*    (2006.01)

(52) U.S. Cl.
USPC ........... 600/568; 606/130; 606/181; 606/185; 600/562; 600/567; 600/573; 600/576

(58) Field of Classification Search
USPC ......... 600/562, 564, 565, 566, 567, 568, 583, 600/584; 606/130, 167, 170, 171, 185, 186
See application file for complete search history.

(56) References Cited

U.S. PATENT DOCUMENTS

| 4,817,631 A | 4/1989 | Schnepp-Pesch et al. |
| 5,078,140 A * | 1/1992 | Kwoh .......................... 600/417 |

(Continued)

FOREIGN PATENT DOCUMENTS

| KR | 10-2007-0028402 A | 3/2007 |
| WO | WO 86/06951 A1 | 12/1986 |

OTHER PUBLICATIONS

Kwang-Gi Kim et al., "Robot System Development for Injection Device of the CT-Guided Lung Biopsy," The Korea Medical Robot Conference, The 2$^{nd}$ Academic Conference, Sep. 5, 2009, pp. 53-54.

*Primary Examiner* — Rene Towa
*Assistant Examiner* — Adam Eiseman
(74) *Attorney, Agent, or Firm* — Foley & Lardner LLP; Michel Morency; Kevin M. Henry

(57) ABSTRACT

Provided is an apparatus for inserting a needle capable of obtaining automation of tissue sample collection or drug injection and operation stability by applying a link mechanism between a needle inserted into a specific part of a human body and a power source for providing a drive force. The apparatus includes a needle unit inserted into a human body, a drive unit configured to provide a drive force to the needle unit such that the needle unit reciprocates between an insertion position at which the needle unit is inserted into the human body and a withdrawal position at which the needle unit is withdraw to the outside of the human body, and a guide unit including a plurality of guide links each having at least two links relatively rotated by the drive force of the drive unit and radially disposed around the needle unit, and configured to guide the needle unit such that the needle unit translates between the insertion position and the withdrawal position in a longitudinal direction of the needle unit.

10 Claims, 8 Drawing Sheets

(56) References Cited

U.S. PATENT DOCUMENTS

| | | | |
|---|---|---|---|
| 5,170,790 A * | 12/1992 | Lacoste et al. | 600/437 |
| 5,938,679 A * | 8/1999 | Freeman et al. | 606/181 |
| 6,210,421 B1 * | 4/2001 | Bocker et al. | 606/182 |
| 6,702,805 B1 * | 3/2004 | Stuart | 606/1 |
| 6,858,015 B2 * | 2/2005 | List | 600/583 |
| 7,175,635 B2 * | 2/2007 | Loser | 606/130 |
| 7,955,321 B2 * | 6/2011 | Kishi et al. | 606/1 |
| 8,062,288 B2 * | 11/2011 | Cooper et al. | 606/1 |
| 2004/0127928 A1 * | 7/2004 | Whitson et al. | 606/181 |
| 2008/0269639 A1 * | 10/2008 | Korner et al. | 600/583 |

* cited by examiner

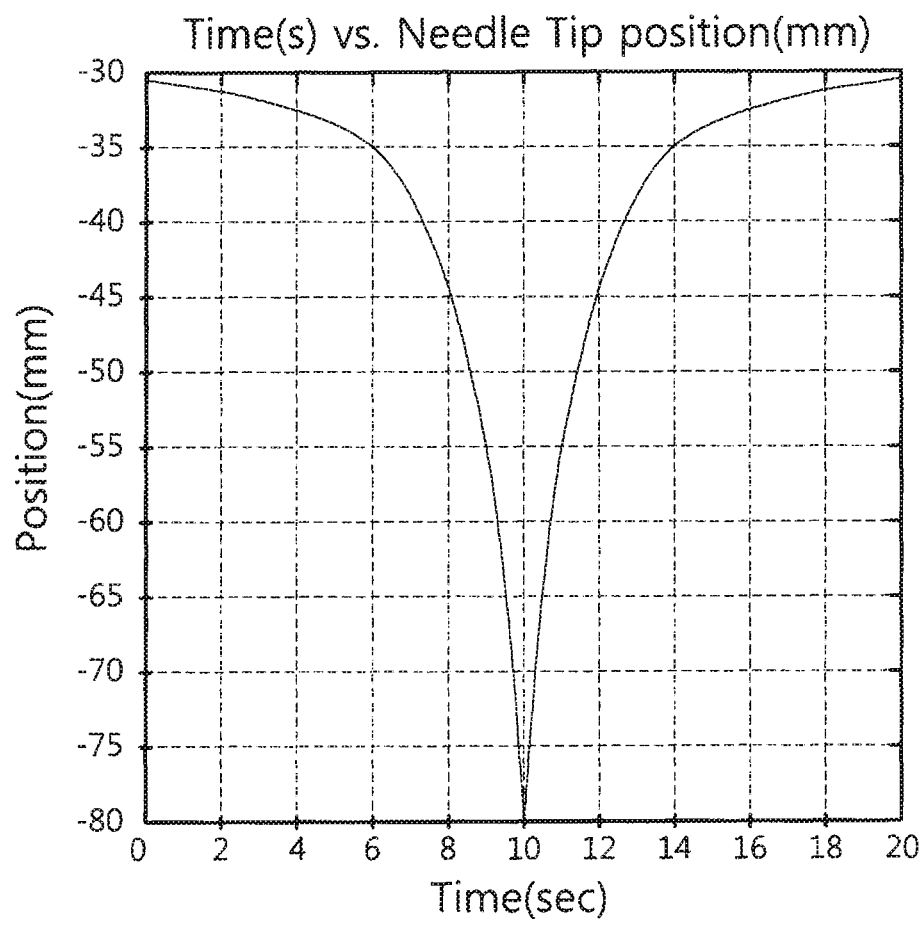

APPARATUS FOR INSERTING NEEDLE

CLAIM FOR PRIORITY

This application claims priority to Korean Patent Application No. 2009-0125831 filed on Dec. 17, 2009 in the Korean Intellectual Property Office (KIPO), the entire contents of which are hereby incorporated by reference.

BACKGROUND

1. Technical Field

Example embodiments of the present invention relate to an apparatus for automatically inserting a needle, and more particularly, to an apparatus for inserting a needle, which is inserted into a human body to collect a tissue sample or insert drugs.

2. Related Art

In general, a biopsy is a surgical procedure for collecting a sample to determine whether a tumor is a benign or malignant tumor, when the tumor has been detected in a human body through radiographic image inspection such as computed tomography (CT), magnetic resonance imaging (MRI), etc. The biopsy has been used to collect tissue by inserting a long needle into a tumor and suctioning tissue of the tumor.

In the biopsy, progression of the needle may not follow a straight path, contrary to expectations, due to differences in softness according to depths of tissues of a human body. In addition, the biopsy must be performed to avoid sensitive areas such as bones, arteries, etc., during insertion of the needle.

For this reason, during the biopsy, an insertion point of a needle end must be checked by frequently obtaining radiographic images during an operation so that a long needle for biopsy can be inserted into a tumor in a human body, which cannot be seen from the exterior with the naked eye. However, an operator in full charge of the biopsy may have a high probability of damage in physical and mental health due to repeated radioactive contacts.

A needle insertion apparatus is an apparatus for automatically inserting a needle into a human body to perform a biopsy or inject drugs. Such a needle insertion apparatus inserts the needle into a part of the human body in which tissue sample collection or drug injection is needed according to analysis results through a radiographic imaging apparatus, etc. That is, the needle insertion apparatus automatically inserts the needle into a corresponding part of the human body after the part of the human body in which insertion of the needle is needed is determined through the radiographic imaging apparatus.

In the case of a biopsy operation, since a needle end must accurately arrive at a specific part of a human body, renewal of image information by the radiographic imaging apparatus is essential. In addition, since the number of radioactive ray transmissions and times are increased to determine a specific part of the human body, the needle can be inserted at a position spaced apart from a radioactive ray transmission space by the needle insertion apparatus, not directly inserted by an operator, thereby increasing efficiency of the operation.

The needle insertion apparatus may be remotely or automatically controlled so that an operator can operate the apparatus at a position spaced apart from the radioactive ray transmission space. Here, the needle insertion apparatus is stably driven by a power source such as an electric motor, a pneumatic piston, etc., for remote control or automatic operation.

A conventional needle insertion apparatus is directly connected to and operated by a power source such as an electric motor, a pneumatic piston, etc., so that power from the power source is directly transmitted to the tissue in the human body through the needle. A mechanism of the conventional needle insertion apparatus may cause pain and damage to a diseased part during a process of passing through the skin and muscle tissues of the human body. In addition, the mechanism of the conventional needle insertion apparatus may be too complicated to adjust the needle insertion speed or force.

SUMMARY

Accordingly, example embodiments of the present invention are provided to substantially obviate one or more problems due to limitations and disadvantages of the related art.

Example embodiments of the present invention provide an apparatus for inserting a needle having a mechanism capable of gradually varying the insertion speed and force depending on an insertion depth of a needle during insertion of the needle into a human body, relatively simplifying the size and mechanism, and effectively improving clinical characteristics.

Example embodiments of the present invention also provide an apparatus for inserting a needle having an improved operational structure capable of controlling adjustment of the needle insertion force and speed.

Additional aspects of the invention will be set forth in the description which follows, and in part will be apparent from the description, or may be learned by practice of the invention.

In some example embodiments, an apparatus for inserting a needle includes: a needle unit inserted into a human body; a drive unit configured to provide a drive force to the needle unit such that the needle unit reciprocates between an insertion position at which the needle unit is inserted into the human body and a withdrawal position at which the needle unit is withdraw to the outside of the human body; and a guide unit including a plurality of guide links each having at least two links relatively rotated by the drive force of the drive unit and radially disposed around the needle unit, and configured to guide the needle unit such that the needle unit translates between the insertion position and the withdrawal position in a longitudinal direction of the needle unit.

The plurality of guide links may be disposed around the needle unit at predetermined angular intervals in a circumferential direction.

At least three guide links may be provided to be radially disposed around the needle unit.

The drive unit may include a motor; a drive shaft connected to the motor and rotated by a drive force provided from the motor; and a driver connected between the drive shaft and the guide unit to be reciprocated in an axial direction of the drive shaft depending on rotation of the drive shaft.

The drive shaft and the driver may be coupled in a ball-screw type such that the driver straightly moves in an axial direction of the drive shaft depending on rotation of the drive shaft.

The guide unit may further include a guide ring connected to any one of at least two links included in the plurality of guide links to reciprocate in a longitudinal direction of the link.

The guide ring may be connected to the driver to move depending on reciprocal movement of the driver, and the guide link may be rotated such that the needle unit reciprocates between the insertion position and the withdrawal position depending on reciprocal movement of the guide ring.

The apparatus may further include a base configured to support at least one of the drive unit and the guide unit. The guide link may include a first link rotatably supported by the base and connected to the guide link; and a second link having one side relatively rotatably connected to the first link and the other side rotatably connected to the needle unit.

The first link may have a guide slot formed in a longitudinal direction thereof, and the guide ring may have a guide pin inserted into the guide slot to move along the guide slot.

When the guide ring moves in the longitudinal direction of the first link, a moving distance of the needle unit may be larger than that of the guide ring.

The needle unit may include a housing rotatably connected to the guide link; a needle inserted into the human body; and a needle receiving part configured to receive a portion of the needle and detachably coupled inside the housing.

The needle unit may further include a detachable coupling member provided in at least one of the housing and the needle receiving part to detachably couple the housing and the needle receiving part.

In other example embodiments, an apparatus for inserting a needle includes: a needle unit having a needle inserted into a human body and a housing for receiving the needle unit; a drive unit configured to provide a drive force to the needle unit such that the needle unit reciprocates between an insertion position at which the needle unit is inserted into the human body and a withdrawal position at which the needle unit is withdrawn to the outside of the human body; a plurality of guide links each having at least two links connected to the needle unit to be relatively rotated with each other, and radially disposed around the needle unit; and a guide ring interposed between at least one of the plurality of guide links and the drive unit to reciprocate in a longitudinal direction of the guide link such that the needle unit translates between the insertion position and the withdrawal position by a drive force from the drive unit in a longitudinal direction of the needle unit.

Here, the needle may be detachably coupled inside the housing.

Specific descriptions of other example embodiments will be apparent from the detailed description and the attached drawings.

BRIEF DESCRIPTION OF THE DRAWINGS

Example embodiments of the present invention will become more apparent by describing in detail example embodiments of the present invention with reference to the accompanying drawings, in which:

FIG. 8 is a graph showing variation in speed, in which variation in position of the needle insertion apparatus with respect to a time is represented as a speed.

DETAILED DESCRIPTION OF EXAMPLE EMBODIMENTS

Figure 1:
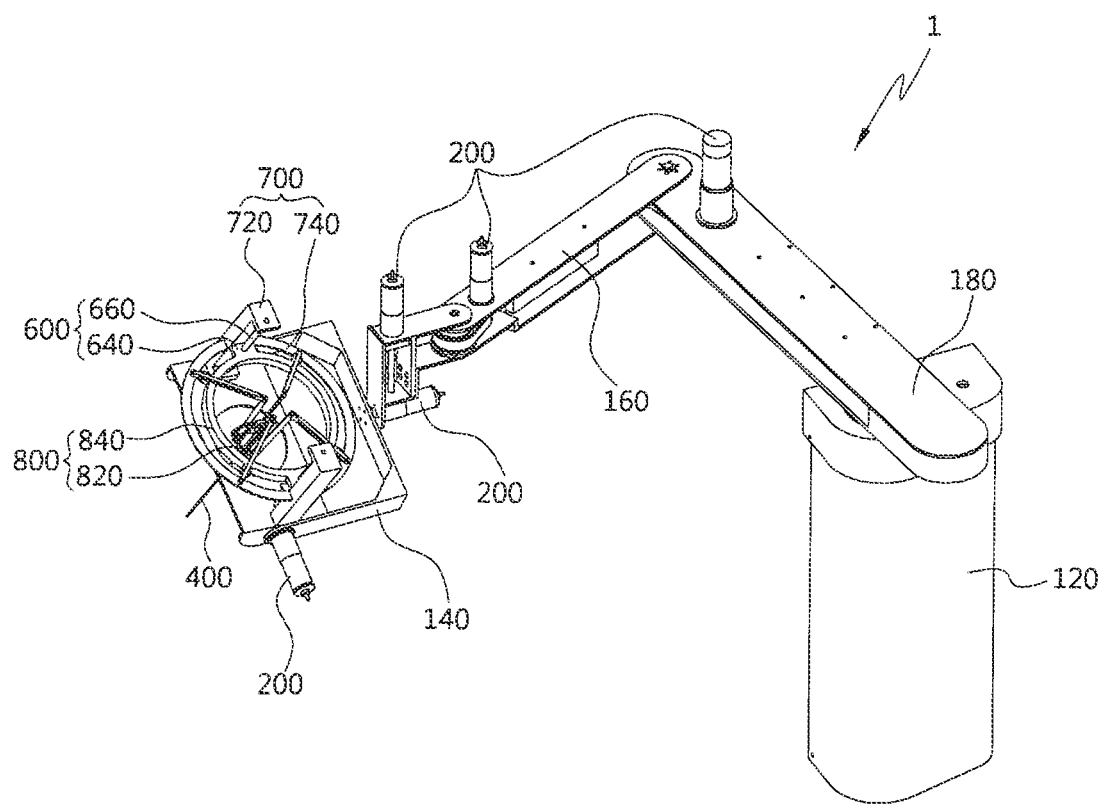
FIG. 1 is a perspective view of an apparatus for inserting a needle in accordance with an example embodiment of the present invention.

Hereinafter, example embodiments of the present invention will be described in detail. However, the present invention is not limited to the embodiments disclosed below, but can be implemented in various forms. The following embodiments are described in order to enable those of ordinary skill in the art to embody and practice the present invention. Like reference numerals designate like elements throughout the detailed description. In the detailed description, if it is determined that description of conventional functions or constitutions may make the spirit of the invention unclear, detailed description thereof will be omitted.

Hereinafter, an apparatus for inserting a needle in accordance with an example embodiment of the present invention will be mainly described to include major components and characteristics, i.e., a needle unit, a drive unit, and a guide unit.

Figure 2:
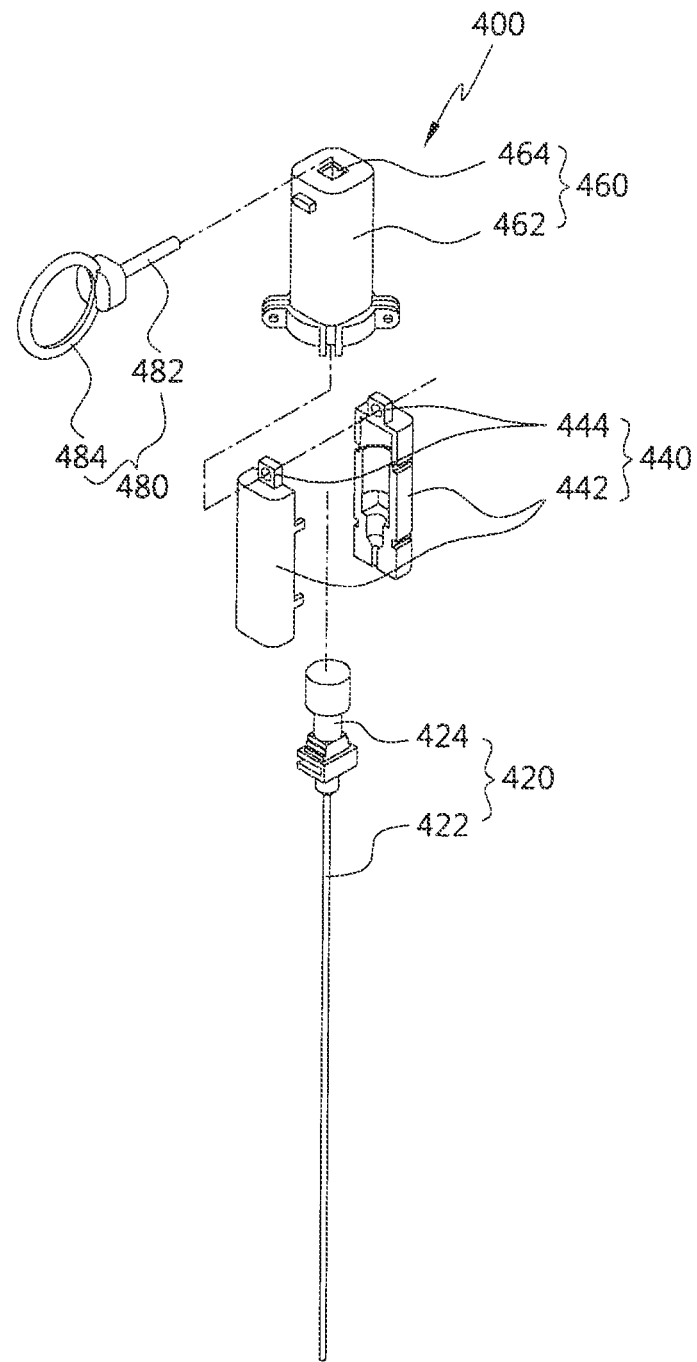
FIG. 2 is an exploded perspective view of major parts of the apparatus for inserting a needle of the present invention.
Figure 3:
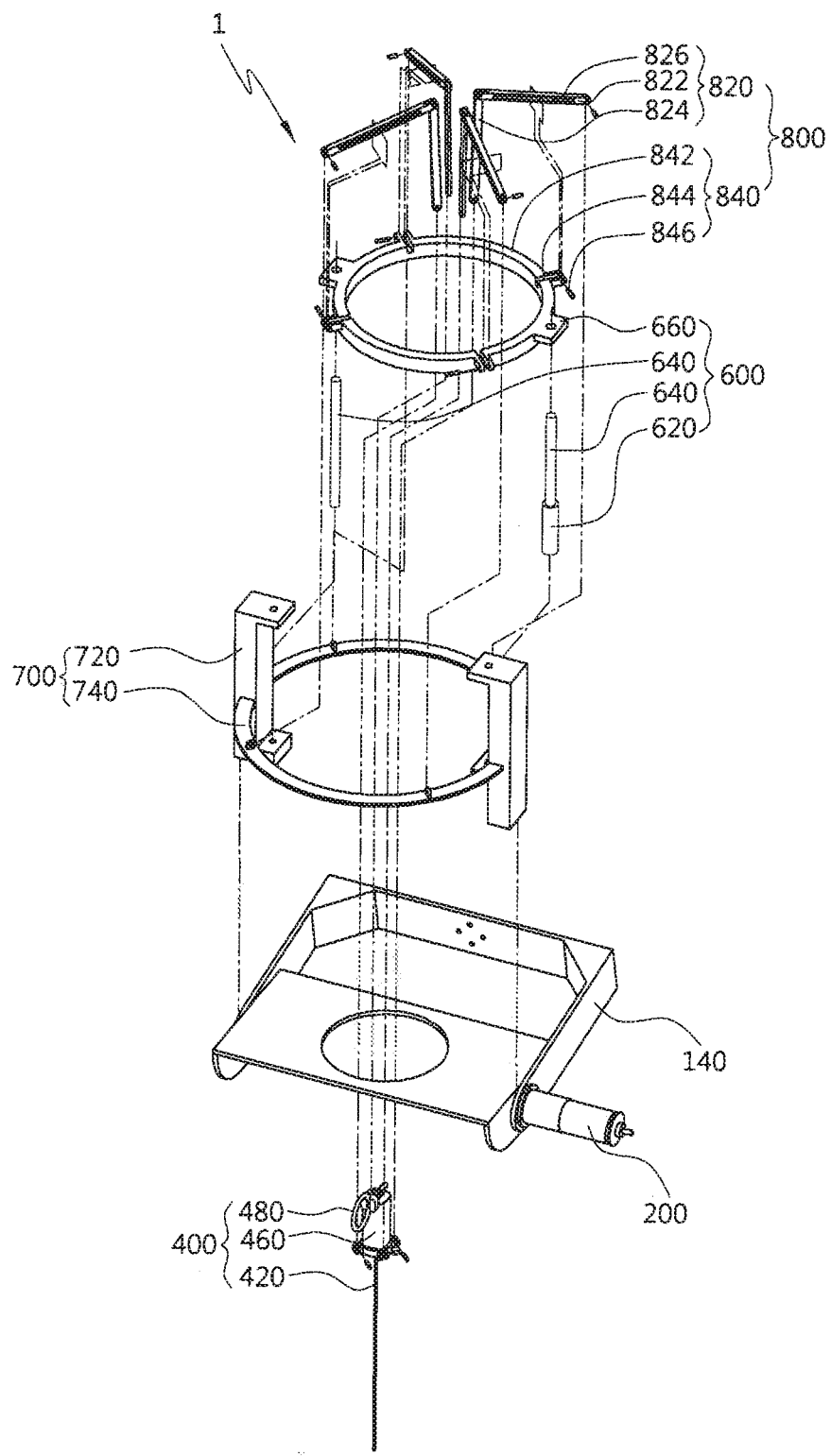
FIG. 3 is an exploded perspective view of a needle unit shown in FIGS. 1 and 2.

FIG. 1 is a perspective view of an apparatus for inserting a needle in accordance with an example embodiment of the present invention, FIG. 2 is an exploded perspective view of major parts of the apparatus for inserting a needle of the present invention, and FIG. 3 is an exploded perspective view of a needle unit shown in FIGS. 1 and 2.

As shown in FIGS. 1 to 3, an apparatus 1 for inserting a needle in accordance with an example embodiment of the present invention includes a main body 100, a main driver 200, a needle unit 400, a drive unit 600, a base 700, and a guide unit 800.

The main body 100 includes a first support 120, a second support 140, a first arm 160, and a second arm 180. The main body 100 supports operations of the needle unit 400 so that the needle unit 400 is inserted into or withdrawn from a patient's tissue. The first support 120 is disposed at one side of a bed (not shown), on which a patient who needs a biopsy or drug injection can lie. In addition, the second support 140 is provided to support the needle unit 400, the drive unit 600, and the guide unit 800.

The first and second arms 160 and 180 are rotatably connected to each other and connected to the second and first supports 140 and 120, respectively. The first and second arms 160 and 180 are relatively rotated to locate the needle unit 400 at a specific part of a patient's body.

The main driver 200 provides drive forces to the first and second arms 160 and 180 so that the first and second arms 160 and 180 are separately rotated, respectively. The main driver 200 in accordance with an example embodiment of the present invention includes an electric motor for generating a drive force, and a belt connected to the electric motor. Of course, the main driver 200 may be provided in various known driver types such as chains, etc., in addition to the belt.

Next, the needle unit 400 is inserted into a specific part of a human body to perform any one of tissue sample collection and drug injection. The needle unit 400 of the present invention includes a needle 420, a needle receiving part 440, a housing 460, and a detachable coupling member 480. The needle unit 400 may be formed of a biocompatible material because it is directly inserted into a specific part of a human body.

The needle 420 of the present invention includes an insertion part 422 inserted into a specific part of a human body, and a head 424 connected to one end of the insertion part 422 and received in the needle receiving part 440. The insertion part 422 of the needle 420 has a hollow bar shape to be inserted into a specific part of a human body to perform any one of tissue sample collection and drug injection.

For example, when the needle 420 is completely inserted into a specific part of a human body, a tissue collecting needle or a drug injector is connected to a hollow region of the needle 420 to perform any one of tissue sample collection or drug injection through the hollow region of the needle 420. The head 424 is received in the needle receiving part 440 to be detachably coupled to the housing 460 of the needle unit 400.

The needle receiving part 440 receives a portion of the needle 420 and is detachably coupled inside the housing 460. The needle receiving part 440 of the present invention includes a receiving body 442 and a projection 444.

The receiving body 442 forms the outside of the needle receiving part 440. The head 424 of the needle 420 is received in the receiving body 442. In one embodiment of the present invention, the receiving body 441 is formed of a pair of halves coupled to each other with the head 424 surrounded therebetween. The receiving body 442 has a shape corresponding to the inside of the housing 460 to be detachably coupled inside the housing 460.

The projection 444 projects from one side of the receiving body 442 opposite to the needle 420 received in the receiving body 442. The projection 444 projects through a through-hole 464 of the housing 460, and has an insertion hole through which the detachable coupling member 480 is inserted. The projection 444 is fixed by the detachable coupling member 480 to secure the needing receiving part 440 to the housing 460. On the other hand, when the detachable coupling member 480 is detached from the projection 444, the needle receiving part 440 may be separated from the housing 460.

The housing 460 is rotatably coupled to a plurality of guide links 820. The housing 460 of the present invention is detachably coupled to the needle receiving part 440 to which the needle 420 is coupled. The housing 460 includes a housing body 462 and the through-hole 464.

In one embodiment of the present invention, the housing body 462 has a cylindrical shape. Four guide links 820 are rotatably connected around the cylindrical housing 460 at predetermined intervals in a circumferential direction. While the housing body 462 in accordance with an example embodiment of the present invention has a cylindrical shape, the housing body 462 may have various shapes such as a rectangular shape, etc., according to disposition of the guide links 820. The needle receiving part 440 is detachably coupled inside the housing body 462.

The through-hole 464 is formed to pass through an upper region of the housing 460 opposite to the needle receiving part 440 detachably coupled to the housing 460. The through-hole 464 is formed such that the projection 444 of the needle receiving part 440 projects therethrough.

The detachable coupling member 480 is inserted into the projection 444 of the needle receiving part 440 projecting through the through-hole 464 of the housing 460 to maintain a coupled state between the housing 460 and the needle receiving part 440. In addition, the detachable coupling member 480 may separate the housing 460 from the needle receiving part 440. The detachable coupling member 480 includes an insertion part 482 and a gripping part 484.

The insertion part 482 is inserted into the projection 444 to maintain a coupled state of the housing 460 and the needle receiving part 440. The insertion part 482 has a bar shape to be inserted into the insertion hole of the projection 444. Of course, a cross-sectional shape of the insertion part 482 may correspond to the shape of the insertion hole of the projection 444.

The gripping part 484 is provided at one end of the insertion part 482 to obtain separation convenience of the insertion part 482 from the projection 444. That is, the gripping part 484 is gripped by an operator so that the insertion part 482 can be separated from the projection 444 by the operator. The gripping part 484 in accordance with an example embodiment of the present invention is formed of an annular ring. However, the gripping part 484 may have various shapes such as a rectangular ring, etc., that can be gripped by an operator.

Next, the drive unit 600 provides a drive force such that the needle unit 400 can reciprocate between an insertion position at which the needle unit 400 is inserted into a specific part of a human body and a withdrawal position at which the needle unit 400 inserted into the specific part of the human body is withdrawn. The drive unit 600 of the present invention includes a motor 620, a drive shaft 640, and a driver 660.

The motor 620 generates a drive force such that the needle unit 400 reciprocates between the insertion and withdrawal positions for insertion and withdrawal of the needle unit 400. The motor 620 of the present invention is an electric motor 620 using electricity as a power source in consideration of the size and weight of the entire needle insertion apparatus 1.

The drive shaft 640 is connected to the motor 620 to be driven by a drive force provided from the motor 620. The drive shaft 640 in accordance with an example embodiment of the present invention is disposed on a drive unit support 720 of the base 700, which will be described. That is, two drive shafts 640 may be provided to be disposed at two drive unit supports 720, respectively. Here, in one embodiment of the present invention, the motor 620 is connected to one of the drive shafts 640 to provide a drive force to the drive shaft 640. Of course, the motor 620 may be connected to the two drive shafts 640.

The driver 660 is connected between the drive shaft 640 and the guide unit 800 to be reciprocated in an axial direction of the drive shaft 640 depending on rotation of the drive shaft 640. The driver 660 converts rotation of the drive shaft 640 into straight movement to provide it to the guide unit 800. The driver 660 of the present invention is integrally formed with the guide unit 800. However, the driver 660 may be separately formed from the guide unit 800 to be coupled to the guide unit 800.

Meanwhile, the drive shaft 640 and the driver 660 are coupled to each other in a ball-screw type to convert rotation of the drive shaft 640 into straight movement of the drive part 640.

The base 700 is provided to support the drive unit 600 and the guide unit 800. The base 700 of the present invention includes the drive unit support 720 and a base rim 740. The base 700 supports the drive unit 600 and the guide unit 800 such that a drive force generated from the drive unit 600 is uniformly transmitted to the needle unit 400.

The drive unit support 720 is provided to support the motor 620 and the drive shaft 640 of the drive unit 600. The drive unit support 720 supports rotation of the drive shaft 640. The drive unit support 720 may be provided as a pair at opposite positions to support both sides of a guide ring 840 of the guide unit 800.

The base rim 740 supports the plurality of guide links 820 receiving a drive force from the drive unit 600 to be rotated. The base rim 740 is disposed at an outer region of a reciprocal movement range of the guide ring 840. The base rim 740 connects the pair of drive unit supports 720 to each other. The base rim 740 has a circular shape corresponding to the guide ring 840 having a circular shape. However, provided that the guide links 820 can be disposed at predetermined intervals, the base rim 740 may have various shapes, such as a rectangular shape, etc.

Figure 4:
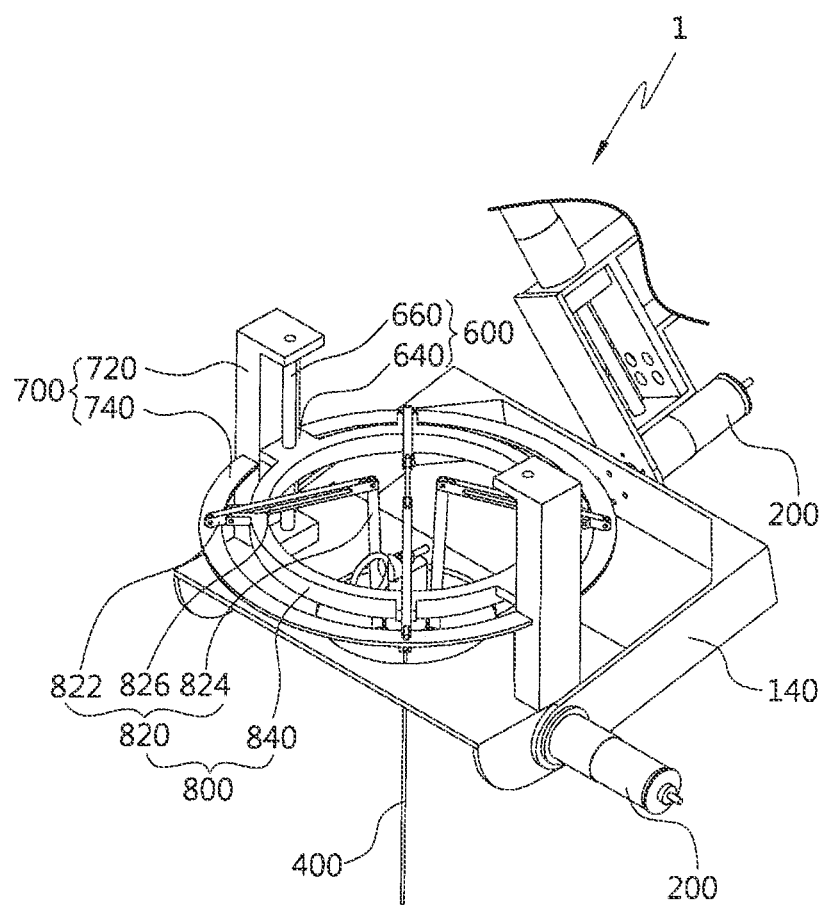
FIG. 4 is a perspective view showing a first operation in which the needle insertion apparatus of the present invention is disposed at a withdrawal position.
Figure 5:
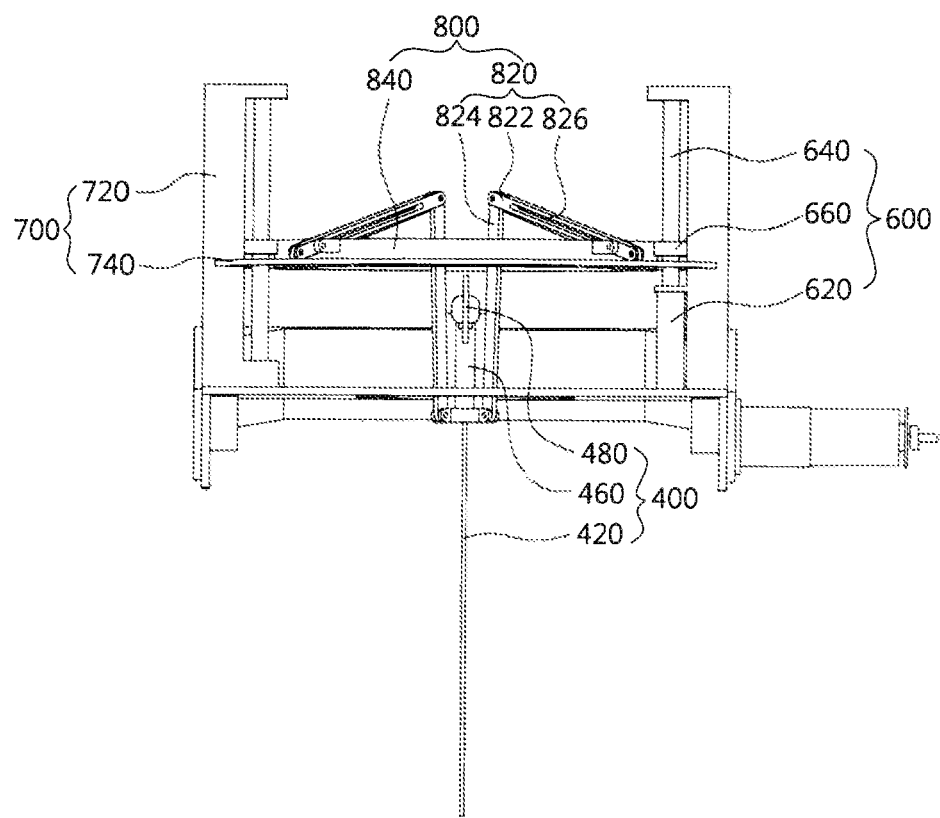
FIG. 5 is a perspective view showing a second operation in which the needle insertion apparatus of the present invention is disposed at an insertion position.
Figure 6:
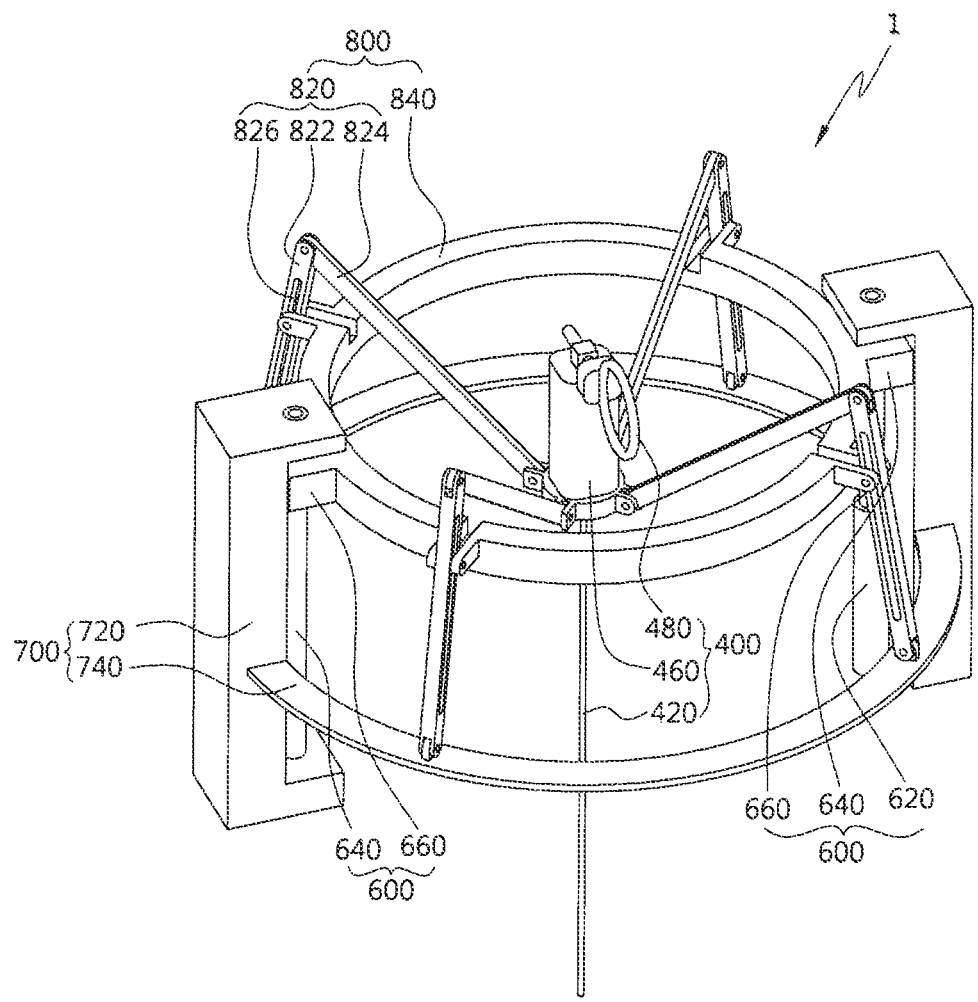
FIG. 6 is a front view of the needle insertion apparatus shown in FIG. 5.

FIG. 4 is a perspective view showing a first operation in which the needle insertion apparatus of the present invention is disposed at a withdrawal position, FIG. 5 is a perspective view showing a second operation in which the needle insertion apparatus of the present invention is disposed at an insertion position, and FIG. 6 is a front view of the needle insertion apparatus shown in FIG. 5.

As shown in FIGS. 4 to 6, the guide unit 800 guides the needle unit 400 such that the needle unit 400 translates between an insertion position and a withdrawal position along a longitudinal direction of the needle unit 400 by a drive force of the drive unit 600. The guide unit 800 of the present invention includes the guide links 820 and the guide ring 840.

The plurality of guide links 820 are radially disposed around the needle unit 400. In one embodiment of the present invention, four guide links 820 are disposed. Of course, the guide links 820 larger or smaller than four may be disposed around the needle unit 400. However, at least three guide links 820 must be disposed in consideration of translation stability of the needle unit 400, i.e., lateral pressure, speed, force, vibration, etc., when the needle unit 400 reciprocates between the insertion position and the withdrawal position.

As described above, the plurality of guide links 820, in which the translation stability of the needle unit 400 is considered, are disposed around the needle unit 400 at predetermined angular intervals in a circumferential direction. For example, four guide links 820 in accordance with an example embodiment of the present invention are disposed at angular intervals of 90°. Here, when at least three guide links 820 are disposed, i.e., when the angular interval is 120°, minimum balance of power can be accomplished to resist the lateral pressure. On the other hand, when the guide links 820 are disposed at angular intervals of 180°, the balance of power may be biased toward one shaft due to translation of the needle unit 400. For this reason, as described above, at least three guide links 820 must be disposed around the needle unit 400 at predetermined angular intervals.

Each of the guide links 820 of the present invention includes a first link 822, a second link 824, and a guide slot 826.

The first link 822 has a bar shape, and is rotatably connected to the second link 824. In one embodiment of the present invention, one side of the first link 822 is rotatably hinged to the base rim 740, and the other side is rotatably connected to one side of the second link 824. In addition, the guide slot 826 is formed in a surface of the first link 822 such that a guide pin 844 of the guide ring 840 is inserted, which will be described below.

The guide slot 826 is formed in a longitudinal direction of the first link 822. The guide slot 826 functions to guide reciprocal movement of the guide ring 840 operated by a drive force of the drive unit 600.

The second link 824 has a bar shape, like the first link 822. One side of the second link 824 is rotatably connected to the first link 822, and the other side is rotatably connected to the needle unit 400. The second link 824 is rotated depending on rotation of the first link 822 caused by reciprocal movement of the guide ring 840.

Meanwhile, when the guide ring 840 moves in a longitudinal direction of the first link 822, a moving distance of the needle unit 400 is larger than that of the guide ring 840. When the guide ring 840 reciprocates along the guide slot 826, a rotation range of the first link 822 with respect to the base rim 740 is smaller than that of the second link 824 with respect to the first link 822. That is, since the rotation range of the second link 824 is larger than that of the first link 822, the moving distance of the needle unit 400 is larger than that of the guide ring 840. The above will be described in detail with reference to FIGS. 7 and 8 when operation of the needle insertion apparatus 1 in accordance with an example embodiment of the present invention is described.

The guide ring 840 connects the plurality of guide links 820 radially disposed around the needle unit 400 to each other. The guide ring 840 reciprocates along the guide links 820 in a longitudinal direction of the guide links 820 by a drive force of the drive unit 600. The guide ring 840 of the present invention includes a guide ring body 842, a guide pin 844, and a link receiving part 846.

The guide ring body 842 forms the outside of the guide ring 840, and is reciprocated by the drive unit 600. The guide ring body 842 is connected to the driver 660 of the drive unit 600 to receive a drive force from the drive unit 600. The guide ring body 842 of the present invention is integrally formed with the driver 660 of the drive unit 600. However, the guide ring body 842 may be separately formed from the driver 660 to be connected to the driver 660. The guide ring body 842 has an annular ring shape to obtain a region in which the guide links 820 are rotated. When the guide ring body 842 reciprocates in the longitudinal direction of the first link 822, the guide links 820 are rotated such that the needle unit 400 translates between the insertion position and the withdrawal position.

The guide pins 844 are inserted into the guide slots 826 to reciprocate in the guide slots 826. The guide pins 844 are disposed along the surface of the guide ring body 842 to correspond to the plurality of guide links 820.

The link receiving part 846 is recessed in the guide ring body 842 to receive the rotating first link 822. For example, the link receiving part 846 is provided to receive the first link 822 rotated when the needle unit 400 is moved from the withdrawal position to the insertion position. The guide pin 844 is disposed at the link receiving part 846 to guide reciprocal movement of the guide ring body 842 with respect to the guide slot 826 of the first link 822.

Figure 7:
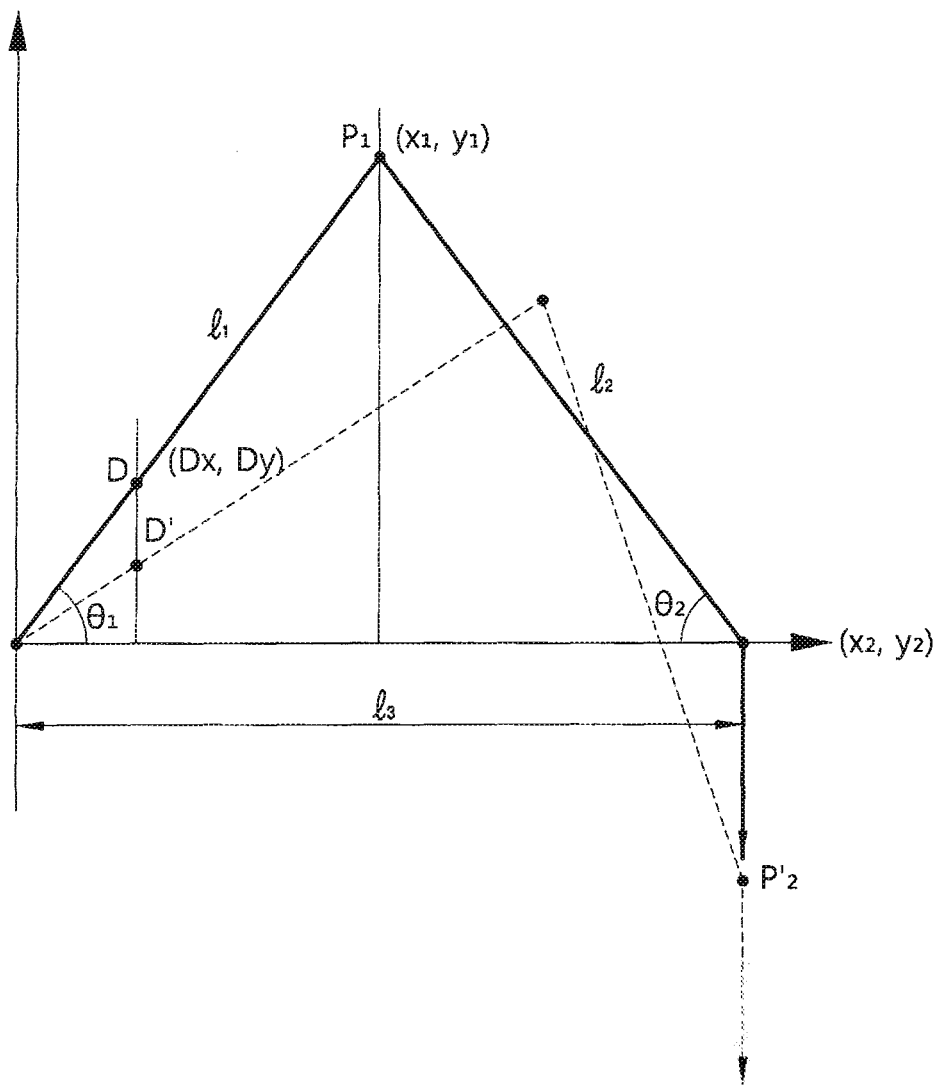
FIG. 7 is a graph for analyzing operations of the needle insertion apparatus in accordance with the present invention.

FIG. 7 is a graph for analyzing operations of the needle insertion apparatus in accordance with the present invention, and FIG. 8 is a graph showing variation in speed, in which variation in position of the needle insertion apparatus with respect to a time is represented as a speed.

Hereinafter, operations of the needle insertion apparatus 1 in accordance with an example embodiment of the present invention will be described in detail with reference to FIGS. 7 and 8.

Specifically, FIG. 7 is a graph for analyzing operations of the first and second links 822 and 824 of the needle insertion apparatus 1 in accordance with an example embodiment of the present invention. It will be appreciated that FIG. 7 shows an initial position (i.e., a withdrawal position) in solid lines and shows an arbitrary position (i.e., an insertion position) upon lowering of the needle unit 400 in dotted lines on a two-dimensional coordinate system to analyze operations of the first and second links 822 and 824.

In addition, in FIG. 7, 0 represents a base point, D represents a contact point at which the first link 822 contacts the guide ring 840 in the withdrawal position, D' represents a contact point at which the first link 822 contacts the guide ring 840 in the insertion position, $P_1$ represents a rotation joint of the first link 822 and the second link 824, $P_2$ represents a rotation joint of the second link 824 and the needle unit 400, and $P_2'$ represents a rotation joint of the second link 824 and the needle unit 400 in the insertion position.

Further, the first link 822 has a length $l_1$, the second link 824 has a length $l_2$, a distance between the base point 0 to $P_2$ is $l_3$, coordinates of D are $(D_x, D_y)$, coordinates of $P_1$ are $(x_1, y_1)$, coordinates of $P_2$ are $(x_2, y_2)$, $\theta_1$ represents an angle between extension lines connecting the first link 822 and points 0 and $P_2$ on the withdrawal position, and $\theta_2$ represents an angle between extension lines connecting the second link 824 and points 0 and $P_2$ on the withdrawal position.

During the operation of the needle insertion apparatus 1 in accordance with an example embodiment of the present invention, a specific part of a human body in which tissue sample collection or drug injection is needed is determined using a radiographic imaging apparatus (not shown) of the present invention.

When the specific part of the human body into which the needle 420 is to be inserted is determined, the main driver 200 of the needle insertion apparatus 1 is driven to position the needle unit 400 to a specific part of a human body.

The drive unit 600 is driven such that the needle unit 400 can be inserted into the specific part of the human body. Then, the driver 660 straightly moves, and thus, the guide ring 840 of the guide unit 800 is lowered.

When the guide ring 840 is lowered, the first and second links 822 and 824 are relatively rotated to translate the needle unit 400 from the withdrawal position to the insertion position.

Since the needle unit 400 is vertically lowered, the following formula is obtained.

$$D_x = l_3 = x_2 = \text{constant}, D_y \geq 0 \quad (1)$$

By a triangle proportional relationship, $$D_x : x_1 = D_y : y_1 \quad (2)$$

is obtained, and when 0 is an origin on a two-dimensional coordinate system, the following relationship is obtained.

$$l_3 = l_1 \cos\theta_1 + l_2 \cos\theta_2$$

$$y_2 = l_1 \sin\theta_1 - l_2 \sin\theta_2$$

$$D_y = D_x \tan\theta_1 \quad (3)$$

A left side of the following formula is obtained by the Pythagoras' theorem, and substituting the formula (2) for this formula, a right side is obtained.

$$l_2^2 - (l_3 - l_1 \cdot \cos\theta_1)^2 = \left(\frac{D_y}{D_x} \cdot l_1 \cdot \cos\theta_1 - y_2\right)^2 \quad (4)$$

Substituting the formula (3) for the formula (4), the following formula is obtained.

$$y_2 = \frac{D_y}{D_x} \cdot l_1 \cdot \cos\left(\tan^{-1}\left(\frac{D_y}{D_x}\right)\right) - \sqrt{l_2^2 - \left(l_3 - l_1 \cdot \cos\left(\tan^{-1}\left(\frac{D_x}{D_y}\right)\right)\right)^2} \quad (5)$$

Eventually, the above formula shows the coordinate relationship of positions vertically lowered from $P_2$ to $P_2'$ with respect to positions vertically lowered from D to D'.

Results shown in FIG. 8 can be obtained through the above formula.

When a moving distance of the needle unit 400 is set from −30 mm to −80 mm, a distance between the insertion position and the withdrawal position of the needle unit 400 is lowered by 50 mm.

Reviewing the graph of the moving distance with respect to the time shown in FIG. 8, it will be appreciated that, when the guide ring 840 of the drive unit 600 is vertically lowered at a certain speed for 10 seconds, a position of a tip of the needle 420 is vertically lowered by 50 mm, and the speed at this time is gradually increased depending on the vertical downward moving speed. The graph from 10 seconds to 20 seconds shown in FIG. 8 shows a symmetrical mechanism by which the needle unit 400 is returned to the withdrawal position from the insertion position.

Meanwhile, when the needle unit 400 is inserted into a specific part of a human body through the above process, an operator removes the detachable coupling member 480 from the needle receiving part 440 to release the coupling of the detachable coupling member 480 to the needle receiving part 440. In addition, a drive force of the main driver 200 is generated to move the needle insertion apparatus 1, except for the needle 420 inserted into a specific part of a human body 420 and the needle receiving part 440. At this time, the insertion state of the needle 420 and the needle receiving part 440 is maintained at the specific part of the human body.

Here, when a biopsy is performed, a needle for collection (not shown) is inserted through the needle 420 inserted into a specific part of a human body to collect tissue samples. On the other hand, in the case of drug injection, a drug injector (not shown) is connected to the specific part through the needle 420.

As can be seen from the foregoing, a guide unit including a guide link having at least two links and disposed in a radial direction with respect to a needle unit and a guide ring for transmitting a drive force to the guide link is applied to generate a thrust force caused by the link connection and to provide resistance against lateral pressure or impact due to a symmetrical structure of a single mechanism during insertion of the needle, thereby reducing errors during the operation to increase reliability of products.

In addition, since a needle inserted into a specific part of a human body is connected to a power source via a link structure, not directly connected thereto, to prevent damage to the power source due to abrupt reaction or impact of a living tissue and direct power transmission to the needle, it is possible to reduce pain to the living tissue or probability of damage.

Further, the speed of the needle is gradually increased by insertion movement of a power transmission mechanism having a link structure to attenuate pains of a diseased area into which the needle is inserted.

Furthermore, the needle inserted into a specific part of a human body may be detachably provided to improve operation convenience, readily exchange the needle with a new one, and reduce maintenance costs.

While the example embodiments of the present invention and their advantages have been described in detail, it should be understood that various changes, substitutions and alterations may be made herein without departing from the scope of the invention.

What is claimed is:

1. An apparatus for inserting a needle comprising:
a needle unit configured to be inserted into a human body;
a drive unit configured to provide a drive force to the needle unit such that the needle unit reciprocates between an insertion position at which the needle unit is inserted into the human body and a withdrawal position at which the needle unit is withdrawn to the outside of the human body; and
a guide unit including a plurality of guide links each having at least two links relatively rotated by the drive force of the drive unit and radially disposed around the needle unit, and configured to guide the needle unit such that the needle unit translates between the insertion position and the withdrawal position in a longitudinal direction of the needle unit;

wherein the drive unit comprises:
- a motor;
- a drive shaft connected to the motor and rotated by a drive force provided from the motor; and
- a driver connected between the drive shaft and a guide unit to be reciprocated in an axial direction of the drive shaft depending on rotation of the drive shaft; and wherein the guide unit further comprises a guide ring connected to any one of at least two links included in the plurality of guide links to reciprocate in a longitudinal direction of the link.

2. The apparatus according to claim 1, wherein the plurality of guide links are disposed around the needle unit at predetermined angular intervals in a circumferential direction.

3. The apparatus according to claim 2, wherein at least three guide links are provided to be radially disposed around the needle unit.

4. The apparatus according to claim 1, wherein the drive shaft and the driver are coupled in a ball-screw type such that the driver straightly moves in an axial direction of the drive shaft depending on rotation of the drive shaft.

5. The apparatus according to claim 1, wherein the guide ring is connected to the driver to move depending on reciprocal movement of the driver, and the guide link is rotated such that the needle unit reciprocates between the insertion position and the withdrawal position depending on reciprocal movement of the guide ring.

6. The apparatus according to claim 1, further comprising:
a base unit configured to support at least one of the drive unit and the guide unit, wherein the guide link comprises:
- a first link rotatably supported by the base unit and connected to the guide ring; and
- a second link having one side relatively rotatably connected to the first link and the other side rotatably connected to the needle unit.

7. The apparatus according to claim 6, wherein the first link has a guide slot formed in a longitudinal direction thereof, and the guide ring has a guide pin inserted into the guide slot to move along the guide slot.

8. The apparatus according to claim 6, wherein, when the guide ring moves in the longitudinal direction of the first link, a moving distance of the needle unit is larger than that of the guide ring.

9. The apparatus according to claim 1, wherein the needle unit comprises:
- a housing rotatably connected to the plurality of guide links;
- a needle configured to be inserted into the human body; and
- a needle receiving part configured to receive a portion of the needle and detachably coupled inside the housing.

10. The apparatus according to claim 9, wherein the needle unit further comprises a detachable coupling member provided in at least one of the housing and the needle receiving part to detachably couple the housing and the needle receiving part.

* * * * *